United States Patent [19]

Heymes et al.

[11] 4,260,747

[45] Apr. 7, 1981

[54] NOVEL OXIMES

[75] Inventors: René Heymes, Romainville; André Lutz, Strasbourg, both of France

[73] Assignee: Roussel Uclaf, Paris, France

[21] Appl. No.: 964,517

[22] Filed: Nov. 29, 1978

[30] Foreign Application Priority Data

Dec. 5, 1977 [FR] France ............................. 77 36513

[51] Int. Cl.³ .......................................... C07D 501/56
[52] U.S. Cl. ....................................... 544/27; 544/28; 548/194
[58] Field of Search ........................... 544/27; 424/246

[56] References Cited

U.S. PATENT DOCUMENTS

| | | | |
|---|---|---|---|
| 4,024,137 | 5/1977 | Cook et al. | 544/27 |
| 4,098,888 | 7/1978 | Ochiai et al. | 544/27 |

FOREIGN PATENT DOCUMENTS 856045 6/1977 Belgium .
2727753 3/1978 Fed. Rep. of Germany .

OTHER PUBLICATIONS

Numata et al., Chem. Pharm. Bull., 25(11) 3117–3119 (1977).

*Primary Examiner*—Paul M. Coughlan, Jr.
*Attorney, Agent, or Firm*—Hammond & Littell, Weissenberger and Muserlian

[57] ABSTRACT

Novel syn isomers of 3-substituted-7-amino-thiazolyl-acetamido-cephalosporanic acid compounds of the formula

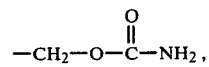

wherein R is selected from the group consisting of alkyl of 1 to 5 carbon atoms, cycloalkyl of 3 to 5 carbon atoms and —CH$_2$—S—R$_1$, R$_1$ is selected from the group consisting of 2-methyl-1,3,4-thiadiazolyl, 1-methyl tetrazolyl, acyl of an organic carboxylic acid of 2 to 4 carbon atoms and

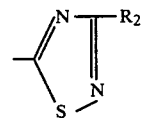

R$_2$ is selected from the group consisting of alkyl and alkoxy of 1 to 4 carbon atoms and A is selected from the group consisting of hydrogen, alkali metal, alkaline earth metal, magnesium and a non-toxic, pharmaceutically acceptable organic amine having antibiotic activity and novel intermediates and process for their preparation.

3 Claims, No Drawings

NOVEL OXIMES

STATE OF THE ART

Various oximes of 3-substituted-7-amino-thiazolyl-acetamido-cephalosporanic acids are described in co-pending, commonly assigned U.S. Patent applications Ser. No. 761,270 filed Jan. 21, 1977 and now abandoned in favor of U.S. Patent application Ser. No. 817,114 filed May 1, 1977, now U.S. Pat. No.4,152,432, Ser. No. 796,315 filed May 12, 1977 as well as Belgium Pat. No. 856,045 and French Pat. No. 2,294,690.

OBJECTS OF THE INVENTION

It is an object of the invention to provide the novel 3-substituted-7-amino-thiazolyl-acetamido-cephalosporanic acids of formula I and novel intermediates and process for their preparation.

It is another object of the invention to provide novel antibiotic compositions and to provide a novel method of combatting bacterial infections in warm-blooded animals.

These and other objects and advantages of the invention will become obvious from the following detailed description.

THE INVENTION

The novel compounds of the invention are the syn isomers of 3-substituted-7-amino-thiazolyl-acetamido-cephalo-sporanic acid compounds of the formula

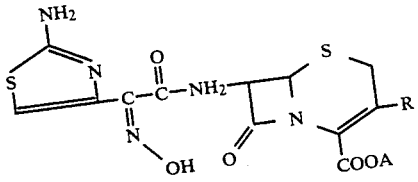

I wherein R is selected from the group consisting of alkyl of 1 to 5 carbon atoms, cycloalkyl of 3 to 5 carbon atoms and $-CH_2-S-R_1$, $R_1$ is selected from the group consisting of 2-methyl-1,3,4-thiadiazolyl, 1-methyl tetrazolyl, acyl of an organic carboxylic acid of 2 to 4 carbon atoms and

$R_2$ is selected from the group consisting of alkyl and alkoxy of 1 to 4 carbon atoms and A is selected from the group consisting of hydrogen, alkali metal, alkaline earth metal, magnesium and a non-toxic, pharmaceutically acceptable organic amine.

Examples of R are alkyl such as methyl, ethyl, propyl, isopropyl, butyl, sec-butyl, tert.-butyl, and pentyl and cycloalkyl such as cyclopropyl, cyclobutyl and cyclopentyl. Examples of $R_2$ are alkyl such as methyl, ethyl, propyl, isopropyl, butyl, sec-butyl and tert.-butyl and alkoxy such as methoxy, ethoxy, propoxy, isopropoxy, butyloxy, sec.-butyloxy and tert.-butyloxy. Examples of $R_1$ as acyl are acetyl, propionyl, n-butyryl and isobutyryl.

Examples of A are hydrogen, alkali metals such as sodium, potassium or lithium, alkaline earth metal such as calcium, magnesium and organic amines such as tri-methylamine, diethylamine, triethylamine, methylamine, propylamine, N,N-dimethyl-ethanolamine, tris-(hydroxymethyl)-aminomethane, arginine or lysine.

Among the preferred compounds of formula I are those wherein R is alkyl of 2 to 5 carbon atoms, those wherein R is cycloalkyl of 3 to 5 carbon atoms, those wherein R is $-CH_2-S-R_1$ and $R_1$ is acyl of an organic carboxylic acid of 2 to 4 carbon atoms and those wherein R is $-CH_2-S-R_1$ and

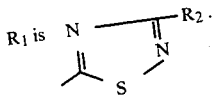

More preferred are the compounds of formula I wherein R is cyclopentyl or those wherein

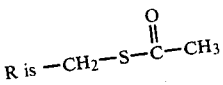

and A is hydrogen and sodium or those wherein R is $-CH_2-S-R_3$ and

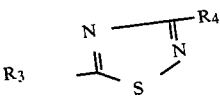

and $R_4$ is methyl or methoxy and A is hydrogen sodium.

Specific preferred compounds of formula I are syn isomer of 3-methyl-7-[2-(2-amino-4-thiazolyl hydroxyimino-acetamido]-ceph-3-eme-4-carboxylic acid and its sodium salt, the syn isomer of 3-[(1-methyl-5-tetrazolyl)-thiomethyl]-7-[2-(2-amino-4-thiazolyl) hydroxyimino-acetamido]-ceph-3-eme-4-carboxyli acid and its sodium salt, the syn isomer of 3-[(2-m 1,3,4-thiadiazol-5-yl)-thiomethyl]-7-[2-(2-amino-4 thiazolyl)-2-hydroxyimino-acetamido]-ceph-3-em carboxylic acid and its sodium salt and the syn iso 3-acetylthiomethyl-7-[2-(2-amino-4-thiazolyl)-2-hydroxyimino-acetamido]-ceph-3-eme-4-carbox acid and its sodium salt.

The compounds of the invention can exist in of formula I or in the following formula

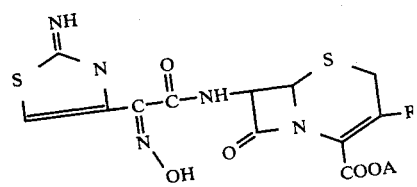

The novel process of the invention for tion of the compounds of formula I comp a compound of the formula

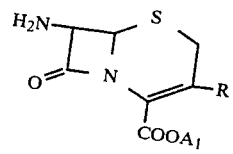

II wherein R has the above definition and $A_1$ is selected from the group consisting of hydrogen and an ester group easily removable by acid hydrolysis of hydrogenolysis with a syn isomer of an acid of the formula

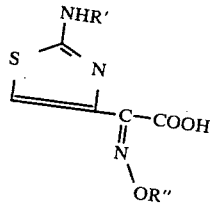

III or a functional derivative thereof wherein R' and R" are selected from the group consisting of a group easily removable by acid hydrolysis or hydrogenolysis and chloroacetyl to obtain a compound of the formula

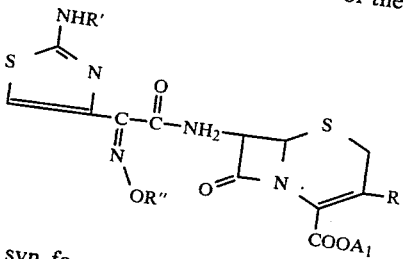

IV e syn form and reacting the latter with an acid olysis agent, a hydrogenolysis agent or thiourea or ality of said agents to obtain the corresponding ound of formula I wherein A is hydrogen which salified, if desired, by the usual methods to obtain responding compound of formula I wherein A is han hydrogen.

ples of groups easily removable by acid hydrohydrogenolysis for R' and R" are tert.-pentyloxyl, tert.-butyloxycarbonyl, trityl, benzyl, benztrichloroethyl, carbonbenzyloxy, formyl, trioxycarbonyl and 2-tetrahydropyranyl. R" be 1-methyl-1-methoxyethyl which is a protecspecific for alcohols. Example of easily resters for $A_1$ by acid hydrolysis or hydrogenolnzhydryl, tert.-butyl, benzyl, p-methoxybenchloroethyl.

erred mode of the latter process, the comrmula II is reacted with a functional derivaacid of formula III such as its acid chloride dride which may be formed in situ by reacbutyl chloroformate or dicyclohexylcarboally useful are other acid halides and other les formed in situ by reaction with other rmates or with a dialkylcarbodiimide or alkylcarbodiimides. Equally useful are vatives such as the acid azide, acid amide r formed, for example, with hydroxysucophenol or 2,4-dinitrophenol. When the product of formula II is effected with an nhydride of formula III, the reaction is ed in the presence of a basic agent such as an alkali metal carbonate or an organic amine such as methyl morpholine, pyridine or a trialkylamine like triethylamine.

The transformation of the compounds of formula IV into the compounds of formula I is effected by replacing R' and R" with hydrogen and replacing $A_1$ when it is an ester group easily removable by acid hydrolysis or hydrogenolysis with hydrogen.

When R' and R" each represent a group easily removable by acid hydrolysis and $A_1$ is hydrogen or an ester group easily removable by acid hydrolysis, one or more acid hydrolysis agents may be used. When R' and R" are each a group easily removable by hydrogenolysis and $A_1$ is hydrogen or an ester group easily removable by hydrogenolysis, one or more hydrogenolysis agents may be used. When R' and/or R" is chloroacetyl, thiourea is used and an acid or hydrogenolysis agent may be used for the values of $A_1$.

An acid, a hydrogenolysis agent and thiourea are used when R' or R" is chloroacetyl and when one of R', R" and $A_1$ are a group easily removable by acid hydrolysis and the other is a group easily removable by hydrogenolysis.

Examples of suitable acid agents are trifluoroacetic acid, formic acid and acetic acid and the acids may be used in anhydrous or aqueous media. Equally useful is the zinc-acetic acid system. Preferably, an acid hydrolysis agent such as anhydrous trifluoroacetic acid or aqueous formic acid or aqueous acetic acid are used to remove trityl, tert.-pentyloxy or tert.-butoxycarbonyl groups for R' and R" or benzhydryl, tert-butyl or p-methoxybenzyl for $A_1$. The zinc-acetic acid system is preferably used to remove trichloroethyl when it is R', R" and $A_1$ and a hydrogenolysis agent such as hydrogen in the presence of a catalyst is used to remove the benzyl for $A_1$ and benzhydryl and carbobenzyloxy groups for R' and R".

The reaction of the compounds of formula IV when R' is chloroacetyl and thiourea is preferably effected in an acid or neutral medium using the procedure of Masaki [J.A.C.S., Vol. 90 (1968), p. 4508]. The salification of the products of formula I may be effected by known methods such as reacting the free acid with a mineral base such as sodium hydroxide, potassium hydroxide or sodium bicarbonate or with a salt of an optionally substituted aliphatic carboxylic acid such as diethylacetic acid, ethylhexanoic acid or especially acetic acid. The sodium salts of the said acids are preferred. The salification can also be effected with an organic base such as triethylamine, diethylamine, trimethylamine, methylamine, propylamine, N,N-dimethylethanolamine, tris(hydroxymethyl)amino- methane, lysine or arginine.

For the preparation of the salts, the solvents of the free acids may also be used in place of the free acids. The salification is preferably effected in one or more solvents such as water, ether, methanol, ethanol or acetone. The salts may be in amorphous or crystalline form depending on the reaction conditions. The crystalline salts are preferably formed by reacting the free acid with a salt of an aliphatic carboxylic acid, preferably sodium acetate. For the sodium salt, the reaction is effected in an appropriate organic solvent such as methanol containing small amounts of water.

In a modification of the process to obtain a compound of the formula

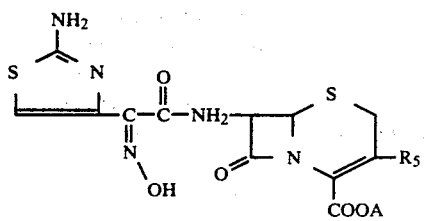

$I_A$ wherein A has the above definition and $R_5$ is selected from the group consisting of alkyl of 1 to 5 carbon atoms, cycloalkyl of 3 to 5 carbon atoms, acetoxymethyl,

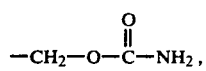

Cl, $CH_3O$— and —$CH_2$—S—$R_1$ where $R_1$ is selected from the group consisting of 2-methyl-1,3,4-thiadiazolyl, 1-methyl-tetrazolyl, acyl of an organic carboxylic acid of 2 to 4 carbon atoms and

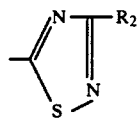

and $R_2$ is selected from the group consisting of alkyl and alkoxy of 1 to 4 carbon atoms comprises reacting a compound of the formula

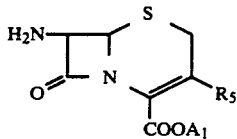

$II_A$ wherein $R_5$ has the above definition and $A_1$ is selected from the group consisting of hydrogen and an ester group easily removable by acid hydrolysis or hydrogenolysis with the syn isomer of an acid of the formula

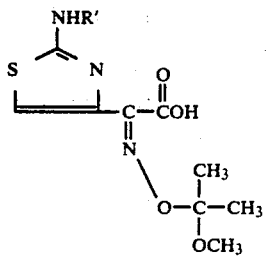

V or a functional derivative thereof wherein R' has the above definition to obtain a compound of the formula in the syn form

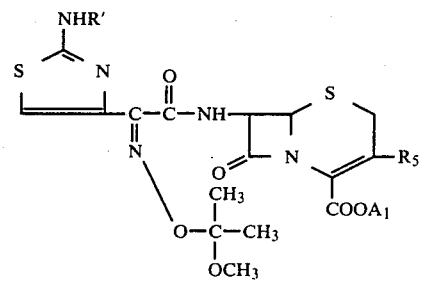

VI and when $A_1$ is hydrogen, the latter may be salified or treated with a derivative of an ester group easily removable by acid hydrolysis or hydrogenolysis and the product of formula VI or its salt may be treated with an aqeuous mineral acid to obtain the syn form of a compound of the formula

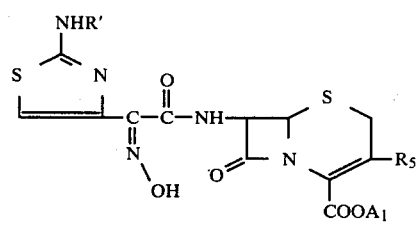

VII which may be treated with a carboxylic acid, a hydrogenolysis agent or thiourea or two of the agents depending on the values of R' and $A_1$ to obtain a compound of formula $I_A$ wherein A is hydrogen or treat the compound of formula VII with an acid hydrolysis agent and depending on the values of R' and $A_1$ with a hydrogenolysis agent or thiourea or both to obtain a compound of formula $I_A$ where A is hydrogen and the latter may be salified to obtain the corresponding salts of formula I.

The reaction of the products of formula $II_A$ and V is effected under the same conditions as the reaction of compounds of formulae II and III. The eventual salification or esterification of the compounds of formula VI is effected in the usual manner such as with diazodiphenylmethane. The aqueous mineral acid is preferably aqueous hydrochloric acid such as N or 2 N hydrochloric acid with reaction at room temperature for one half to several hours. A neutral pH is then obtained by addition of a base such as sodium bicarbonate.

When a carboxylic acid is used to transform the compound of formula VII to a compound of formula $I_A$, an aqueous organic acid such as aqueous formic acid is used. When a carboxylic acid is used to transform directly the compound of formula VI to a compound of formula $I_A$, an aqueous organic acid such as aqueous formic acid and the temperature is preferably greater than room temperature such as about 50° C. with aqueous formic acid. The salification of the products of formula $I_A$ may be effected under the same conditions as described previously.

The novel antibiotic compositions of the invention are comprised of an antibiotically effective amount of at least one compound of formula I and an inert pharmaceutical carrier or excipient. The compositions may be liquids or solids in the usual form such as tablets, dragees, gelules, granules, suppositories, injectable solutions or suspensions, pomades, creams, gels, etc.

Examples of suitable excipients are those usually used such as talc, arabic gum, lactose, starch, magnesium stearate, cacao butter, aqueous and non-aqueous vehicles, fatty bodies of animal or vegetable origin, paraffinic derivatives, glycols, preservatives, diverse wetting agents, dispersants or emulsifiers.

The compositions of the invention have a very good antibiotic activity against gram positive bacteria such as staphylococcus, streptococcus and especially penicillin-resistant staphylococcus and against gram negative bacteria such as coliform bacteria, Klebsiella, Salmonella and Proteus.

The compositions are therefore useful in the treatment of germ sensitive infections and particularly those of staphylococcia such as staphylococcial septicemia, staphylococcia malignant on the face or skin, pyodermatitis, septic or suppurantes sores, anthrax, phlegmons, eresipels, acute primitive or post-grip staphylococcia, bronchopneumania or pulomonary suppurations. They are equally useful for the treatment of collibacillosis and associated infections, infections of Proteus, Klebsiella and Salmonella and other infections caused by gram negative bacteria.

Among the preferred compositions of the invention are those wherein R is alkyl of 2 to 5 carbon atoms, those wherein R is cycloalkyl of 3 to 5 carbom atoms, those wherein R is —CH$_2$—S—R$_1$ and R$_1$ is acyl of an organic carboxylic acid of 2 to 4 carbon atoms and those wherein R is —CH$_2$—S—R$_1$ and

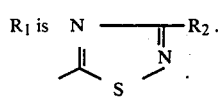

More preferred are the compounds of formula I wherein R is cyclopentyl or those wherein

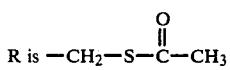

and A is hydrogen and sodium or those wherein R is —CH$_2$—S—R$_3$ and

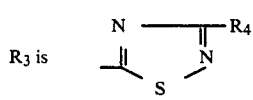

and R$_4$ is methyl or methoxy and A is hydrogen or sodium.

Specific preferred compositions of the invention are those containing as the active ingredient the syn isomer of 3-methyl-7-[2-(2-amino-4-thiazolyl)-2-hydroxyimino-acetamido]-ceph-3-eme-4-carboxylic acid and its sodium salt, the syn isomer of 3-[(1-methyl-5-tetrazolyl)-thiomethyl]-7-[2-(2-amino-4-thiazolyl)-2-hydroxyimino-acetamido]-ceph-3-eme-4-carboxylic acid and its sodium salt, the syn isomer of 3-[(2-methyl-1,3,4-thiadiazol-5-yl)-thiomethyl]-7-[2-(2-amino-4-thiazolyl)-2-hydroxyimino-acetamido]-ceph-3-eme-4-carboxylic acid and its sodium salt and the syn isomer of 3-acetyl-thiomethyl-7-[2-(2-amino-4-thiazolyl)-2-hydroxy-imino-acetamido]-ceph-3-eme-4-carboxylic acid and its sodium salt.

The novel method of the invention of combatting bacterial infections in warm-blooded animals, including humans, comprises administering to warm-blooded animals an antibiotically effective amount of at least one compound of formula I. The compounds may be administered orally, rectally, parenterally, intramuscularly or locally by topical application to the skin or mucous. The usual effective daily dose is dependent on the specific compound and the method of administration. It may be 5 to 80 mg/kg per day in the adult by oral route with the product obtained in Example 3 and 10 to 20 mg/kg thrice a day by intramuscular route with products obtained in Example 3.

The novel intermediates of the invention have the formula

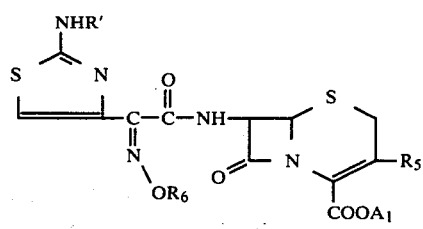

in the syn form wherein R', R$_5$ and A$_1$ have the above definitions and R$_6$ is selected from the group consisting of hydrogen and

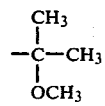

with the proviso that R$_5$ is not acetoxymethyl when R$_6$ is hydrogen.

The compounds of formula II when

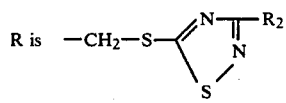

and R$_2$ is alkyl or alkoxy of 1 to 4 carbon atoms may be prepared by an exchange reaction of 7-amino-cephalosporanic acid with a compound of the formula

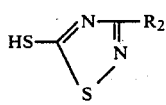

by known methods. The products of formula B which are not known may be prepared by reaction of sodium sulhydrate or sodium thioacetate or thiourea in the presence of potassium hydroxide with a compound of the formula

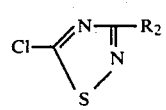

The products of formula V may be prepared by reaction of 2-methoxy-propene and a compound of the formula

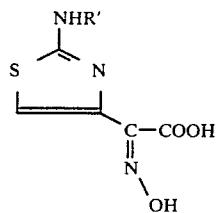

In the following examples there are described several preferred embodiments to illustrate the invention. However, it is to be understood that the invention is not intended to be limited to the specific embodiments.

EXAMPLE 1 syn isomer of 3-methyl-7-[2-(2-amino-4-thiazolyl)-2-hydroxyimino-acetamido]-ceph-3-eme-4-carboxylic acid STEP A: syn isomer of 2-(2-tritylamino-4-thiazolyl)-2-[1-methyl-1-methoxyethoxyimino]-acetic acid A mixture of 12.9 g of the syn isomer of 2-(2-tritylamino-4-thiazolyl)-2-hydroxyimino-acetic acid, 120 ml of methylene chloride and 12 ml of 2-methoxy-propene was stirred at room temperature for 20 minutes and was then evaporated to dryness. The residue was taken up in 60 ml of methylene chloride and 12 ml of 2-methoxy-propene and the mixture was stirred for 30 minutes and evaporated to dryness under reduced pressure to obtain 2.33 g of the syn isomer of 2-(2-tritylamino-4-thiazolyl)-2-(1-methyl-1-methoxy-ethoxyimino-acetic acid which was used as is for the next step.

STEP B: syn isomer of tert.-butyl 3-methyl-7-[2-(2-tritylamino-4-thiazolyl)-2-(1-methyl-1-methoxy-ethoxyimino)-acetamido]-ceph-3-eme-4-carboxylate A solution of 1.25 g of tert.-butyl 7-amino-desacetoxy-cephalosporanate in 2.5 ml of methylene chloride was added to a mixture of the product of Step A in 10 ml of methylene chloride and the mixture was cooled in an ice water bath. A solution of 1.082 g of dicyclohexylcarbodiimide in 10 ml of methylene chloride in a dropping funnel was added over 18 minutes to the mixture at 0° to 5° C. and about 10 minutes later, dicyclohexylurea crystallized. The mixture was stirred at 0° to 5° C. for 30 minutes and the temperature was then allowed to rise over 30 minutes to room temperature. The mixture was then stirred at 20°-25° C. for one hour and after cooling the mixture to 0° to 5° C., 0.93 ml of a molar solution of dicyclohexylcarbodiimide in methylene chloride was added thereto. The mixture was stirred for one hour at 0° to 5° C. and was then vacuum filtered. The product was rinsed with methylene chloride and the filtrate was evaporated to dryness under reduced pressure to obtain 4.622 g of a raw resin. The latter was chromatographed over silica gel and was eluted with a 1-1 benzene-ether mixture to obtain a homogenous fraction which was dried to obtain 2.238 g of the syn isomer of tert.-butyl 3-methyl-7-[2-(2-tritylamino-4-thiazolyl)-2-(1-methyl-1-methoxy-ethoxyimino)-acetamido]-ceph-3-eme-4-carboxylate.

STEP C: syn isomer of 3-methyl-7-[2-(2-amino-4-thiazoyl)-2-hydroxyimino-acetamido]-ceph-3-eme-4-carboxylic acid 2 g of the product of Step B were added with stirring at room temperature to 20 ml of trifluoroacetic acid held under nitrogen and after stirring for 10 minutes at room temperature, the mixture was concentrated under vacuum to a volume of 8 ml. The mixture was cooled in an ice water bath and 60 ml of isopropyl ether were slowly added thereto. The mixture was stirred for 10 minutes at room temperature and was vaccum filtered and the filter was rinsed with isopropyl ether. The filtrate was evaporated to dryness under reduced pressure to obtain 1.5 g of raw product. The latter was placed under an argon atmosphere and 7.5 ml of 50% aqueous formic acid were added thereto. The mixture was stirred at 40° C. for 15 minutes and was then vacuum filtered. The recovered product was rinsed twice with 1 ml of 50% aqueous formic acid and 3 times with 1 ml of distilled water to obtain 319 mg of triphenyl carbinol. The filtrate was distilled to dryness and ethanol was added. The mixture was triturated with 15 ml of ether and was vacuum filtered. The recovered product was rinsed with ether and dried to obtain 0.973 g of the syn isomer of 3-methyl-7-[2-(2-amino-4-thiazolyl)-2-hydroxyimino-acetamido]-ceph-3-eme-4-carboxylic acid with an RF=0.3 (acetone containing 10% water).

EXAMPLE 2 syn isomer of sodium 3-methyl-7-[2-(2-amino-4-thiazolyl)-2-hydroxyimino-acetamido]-ceph-3-eme-4-carboxylate 0.927 g of the product of Example 1 was dissolved in 4.8 ml of a molar solution of sodium acetate in methanol and the solution was vacuum filtered. The filter was rinsed twice with 0.6 ml of the molar solution of sodium acetate in methanol and twice with 0.6 ml of methanol and then 12 ml of absolute ethanol were slowly added to the combined filtrates. The mixture was vacuum filtered at room temperature and the recovered product was rinsed 3 times with 2 ml of ethanol and with ether and was dried to obtain 517 mg of the syn isomer of sodium 3-methyl-7-[2-(2-amino-4-thiazolyl)-2-hydroxyimino-acetamido]-ceph-3-eme-4-carboxylate. The mother liquors were diluted with 6 ml of ethanol to obtain a second yield of 58 mg of the said sodium salt.

RMN Spectrum $(CD_3)_2SO$:1.93 ppm (3-methyl); 6.61 ppm (thiazole proton).

EXAMPLE 3 syn isomer of 3-[(1-methyl-5-tetrazolyl)-thiomethyl]-7-[2-(2-amino-4-thiazolyl)-2-hydroxyimino-acetamido]-ceph-3-eme-4-carboxylic acid STEP A: syn isomer of 3-[(1-methyl-5-tetrazolyl)-thiomethyl]-7-[(2-(2-tritylamino-4-thiazolyl)-2-(1-methyl-1methoxy-ethoxyimino)-acetamido]-ceph-3-eme-4-carobyxlic acid A mixture of 4.3 g of the syn isomer of 2-(2-tritylamino-4-thiazolyl)-2-hydroxyimindo-acetic acid, 25 ml of methylene chloride and 4 ml of 2-methoxy-propene was stirred at room temperature for 20 minutes and was then evaporated to dryness. The residue was taken up in 25 ml of methylene chloride and 1.1 of dicyclohexylcarbodiimide were added thereto. After stirring the mixture at room temperature for 50 minutes, the mixture was vacuum filtered to remove 0.8 g of dicyclohexylurea and the filtrate was cooled to −30° C. A solution of 1.64 g of 3-(1-methyl-5-tetrazolyl-thiomethyl)-7-amino-cephalosporanic acid, 8 ml of methylene chloride and 1.2 ml of triethylamine was added thereto at −30° C. The temperature of the mixture was allowed to return to room temperature over 90 minutes and was then poured into 20 ml of ethyl acetate. The mixture was then stirred for 10 minutes with 20 ml of N hydrochloric acid and was then vacuum filtered to remove excess starting syn isomer. The filtrate was decanted and the organic phase was dried and evaporated to dryness to obtain the syn isomer of 3-[(1-methyl-5-tetrazolyl)-thiomethyl]-7-[2-(2-tritylamino-4-thiazolyl)-2-(1-methyl-1-methoxy-ethoxyimino)-acetamido]-ceph-3-eme-4-carboxylic acid.

STEP B: syn isomer of 3-[(1-methyl-5-tetrazolyl)-thiomethyl]-7-[2-(2-tritylamino-4-thiazolyl)-2-hydroxylimino-acetamido]-ceph-3-eme-4-carboxylic acid 0.5 ml of diethylamine were added to a solution of the product of Step A in 10 ml of ethyl acetate followed by addition of 100 ml of ether. The mixture was vacuum filtered to obtain 2.748 g of the syn isomer of diethylamine 3-[(1-methyl-5-tetrazolyl)-thiomethyl]-7-[2-(2-tritylamino-4-thiazolyl)-2-(1-methyl-1-methoxy-ethoxyimino)-acetamido]-ceph-3-eme-4-carboxylate. A mixture of the said product in 10 ml of acetone and 3.5 ml of N hydrochloric acid was stirred for 40 minutes and the acetone phase was extracted with ethyl acetate. The ethyl acetate phase was dried and evaporated to a small volume. 50 ml of ether were added to effect preceipitation to obtain 1.83 g of the syn isomer of 3-[(1-methyl-5-tetrazolyl)-thiomethyl]-7-[2-(2-tritylamino-4-thiazolyl)-2-hydroxyimino-acetamido]-ceph-3-eme-4-carboxylic acid.

STEP C: syn isomer of 3-[(1-methyl-5-tetrazolyl)-thiomethyl]-7-[2-(2-amino-4-thiazolyl)-2-hydroxyimino-acetamido]-ceph-3-eme-4-carboxylic acid A mixture of the product of Step B and 4 ml formic acid containing 1/3 volume of water was stirred for 10 minutes and was then evaporated to dryness. The residue was triturated with 10 ml of water and was then vacuum filtered. The solid was washed with water and empasted with ether to remove triphenyl carbinol. The raw product was dissolved in 15 ml of acetone containing 20% water and the mixture was vacuum filtered. The product was triturated with 10 ml of ethanol to obtain 1 g of raw product which was empasted with 5 ml of a 1-1 methylene chloride-ethanol mixture to obtain 0.6 g of the syn isomer of 3-[(1-methyl-5-tetrazolyl)-thiomethyl]-7-[2-(2-amino-4-thiazolyl)-2-hydroxyimino-acetamido]-ceph-3-eme-4-carboxylic acid.

Analysis: $C_{15}H_{15}O_5N_9S_3$. 1 $CH_3-CH_2OH$; molecular weight=543.63; Calculated: %C 23.1; %S 17.7; Found: 22.2; 17.7.

RMN Spectrum: $(CD_3)_2SO$ 6.65 ppm (thiazole proton); 7.25 ppm (free amine).

I.R. Spectrum (Nujol): absorption at 1770 cm$^{-1}$ ($\beta$-lactam).

EXAMPLE 4 syn isomer of 3-(acetylthiomethyl)-7-[2-(2-amino-4-thiazoly)-2-hydroxyimino-acetamido]-ceph-3-eme-4-carboxylic acid STEP A: syn isomer of diethylamine 3-acetylthiomethyl-7-[2-(2-tritylamino-4-thiazolyl)-2-(1-methyl-1-methoxyethoxyimino)-acetamido]-ceph-3-eme-4-carboxylate A mixture of 4.3 g of syn isomer of 2-(2-tritylamino-4-thiazolyl)-2-hydroxyimino-acetic acid, 25 ml of methylene chloride and 4 ml of 2-methoxypropene was stirred for 20 minutes at room temperature and was then treated as in Step A of Example 3 to obtain 1.2 g of 3-acetylthiomethyl-3-amino-cephalosporanic acid which was not isolated and treated as in Step B of Example 3 to obtain 2.64 g of the syn isomer of diethylamine 3-acetylthiomethyl-7-[2-(2-tritylamino-4-thiazolyl)-2-(1-methyl-1-methoxy-ethoxyimino)-acetamido]-ceph-3-eme-4-carboxylate.

STEP B: syn isomer of 3-acetylthiomethyl-7-[2-(2-amino-4-thiazolyl)-2-hydroxyimino-acetamido]-ceph-3-eme-4-carboxylic acid The product of Step A was added to a mixture of 10 ml of acetone and 3.5 ml of 2N hydrochloric acid and the acetone was evaporated. The mixture was extracted with ethyl acetate and the ethyl acetate phase was triturated with ether. The mixture was vacuum filtered to obtain the syn isomer of 3-acetylthiomethyl-7-[2-(2-tritylamino-4-thiazolyl)-2-hydroxyimino-acetamido]-ceph-3-eme-4-carboxylic acid which was then stirred with 4 ml of aqueous formic acid (1 volume water - 2 volumes of formic acid) at 45° C. for 10 minutes. The mixture was evaporated to dryness under reduced pressure and the residue was triturated with 5 ml of water. The mixture was vacuum filtered and dried under reduced pressure to obtain 1 g of raw product which was dissolved in 20 ml of ethanol. The mixture was vacuum filtered to remove insolubles and the filtrate was evaporated to half its volume. 20 ml of ethanol were added thereto and the mixture was again evaporated to half its volume. The mixture was vacuum filtered and the product was washed with ethanol and with ether to obtain 0.5 g of purified syn isomer of 3-acetylthiomethyl-7-[2-(2-amino-4-thiazolyl)-2-hydroxyimino-acetamido]-ceph-3-eme-4-carboxylic acid.

Analysis: $C_{15}H_{15}O_6N_5S_3$. 0.5 $CH_3-CH_2-OH$; molecular weight=480.5; Calculated: %N 14.57; %S 20.00; Found: 14.3; 20.1.

I.R. Spectrum (Nujol): absorption at 1776 cm$^{-1}$ ($\beta$-lactam).

RMN Spectrum $(CD_3)_2SO$: 6.66 ppm (thiazole proton).

EXAMPLE 5 syn isomer of 3-acetoxymethyl-7-[2-(2-amino-4-thiazolyl)-2-hydroxyimino-acetamido]-ceph-3-eme-4-carboxylic acid STEP A: syn isomer of diethylamine 3-acetoxymethyl-7-[2-(2-tritylamino-4-thiazolyl)-2-(1-methyl-1-methoxy-ethoxyimino)-acetamido]-ceph-3-eme-4-carboxylate 47.25 g of 2-(2-tritylamino-4-thiazolyl)-2-hydroxyimino-acetic acid were reacted to obtain the syn isomer of 2-(2-tritylamino-4-thiazolyl)-2-(1-methyl-1-methoxy-ethoxyimino)-acetic acid which was dissolved in 230 ml of methylene chloride and then 12.5 g of dicyclohexylcarbodiimide were added thereto. The mixture was stirred for one hour at room temperature and was vacuum filtered to remove the 9.82 g of dicyclohexylurea formed. The filter was rinsed with a little methylene chloride and a solution of 13.6 g of 7-aminocephalosporanic acid in 70 ml of methylene chloride and 14 ml of triethylamine was added to the filtrate. The mixture was stirred for 2 hours at room temperature and was washed with 350 ml of N hydrochloric acid. The organic phase was decanted and was washed with water, dried and evaporated to dryness. The residue was dissolved in 100 ml of ethyl acetate and crystallization was induced. After 30 minutes, the mixture was vacuum filtered to recover 5.5 g of the starting product and the filtrate was evaporated to dryness. The residue was stirred with 200 ml of isopropyl ether for 30 minutes and the mixture was vacuum filtered. The recovered product was dried to obtain 37.35 g of raw product which was dissolved in 148 ml of ethyl acetate and 5.5 ml of diethylamine were added thereto. Precipitation was effected by adding 650 ml of ether with stirring and the mixture was vacuum filtered. The recovered product was washed with ether and dried to obtain 26.35 g of the syn isomer of diethylamine 3-acetoxymethyl-7-[2-(2-tritylamino-4-thiazolyl)-2-(1-methyl-1-methoxy-ethoxyimino)-acetamido]-ceph-3-eme-4-caroboxylate. The filtrate was evaporated to dryness and the residue was taken up in 50 ml of ether to obtain an additional 2.8 g of the said syn isomer. The product was used as is for the next step.

RMN Spectrum: (CDCl₃-60 MHz):

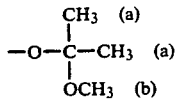

(a) = 1.54 ppm
(b) = 3.27 ppm 6.78 ppm (thiazole proton)

STEP B: syn isomer of diphenylmethyl 3-acetoxymethyl-7-[2-(2-tritylamino-4-thiazolyl)-2-(1-methyl-1-methoxy-ethoxyimino)-acetamido]-ceph-3-eme-4-carboxylate A mixture of 4.15 g of the product of Step A, 40 ml of methylene chloride and 55 ml of 0.1 N hydrochloric acid was stirred at room temperature for 10 minutes and was then decanted. The organic phase was washed twice with 25 ml of water, dried and vacuum filtered. The filter was rinsed with methylene chloride and 15 ml of a solution of 8% diazodiphenyl methane in benzene was added to the filtrate with stirring over 10 minutes. The mixture was stirred for 15 minutes at room temperature and was evaporated to dryness at 30° C. under reduced pressure. The residue was taken up in isopropyl ether and the mixture was vacuum filtered. The product was rinsed and dried to obtain 4.41 g of the syn isomer of diphenylmethane 3-acetoxymethyl-7-[2-(2-tritylamino-4-thiazolyl)-2-(1-methyl-1-methoxy-ethoxyimino)-acetamide]-ceph-3-eme-4-carboxylate.

RMN Spectrum (CDCl₃):

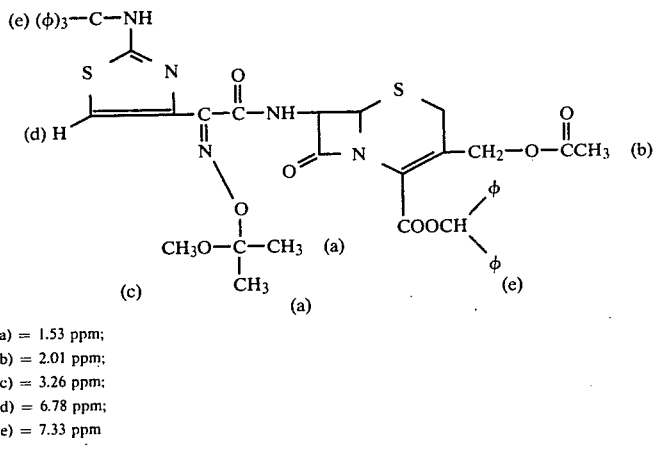

(a) = 1.53 ppm;
(b) = 2.01 ppm;
(c) = 3.26 ppm;
(d) = 6.78 ppm;
(e) = 7.33 ppm

STEP C: syn isomer of diphenylmethyl 3-acetoxymethyl-7-[2-(2-tritylamino-4-thiazolyl)-2-hydroxyimino-acetamido]-ceph-3-eme-4-carboxylate A mixture of 2.775 g of the product of Step B, 14 ml of acetone and 4.5 ml of N hydrochloric acid was stirred for 2 hours at room temperature and then the acetone was evaporated under reduced pressure. 20 ml of ethyl acetate were added to the mixture which was then stirred and decanted. The organic phase was washed 4 times with 10 ml of slightly salified water and the wash waters were extracted with 5 ml of ethyl acetate. The combined organic fractions were dried and vacuum filtered. The filter was rinsed with ethyl acetate and the filtrate was evaporated to dryness under reduced pressure. The residue was taken up in ether, crystallized and efflorcesed. The mixture was vacuum filtered and the recovered product was rinsed with ether and dried to obtain 1.88 g of the syn isomer of diphenylmethyl 3-acetoxymethyl-7-[2-(2-tritylamino-4-thiazolyl)-2-hydroxyimino-acetamido]-ceph-3-eme-4-carboxylate with an Rf=0.5 (ether containing 20% acetone eluant)

RMN Spectrum (CDCl₃-60 MHz): 6.88 ppm (thiazole proton); 7.33 ppm (phenyl ring proton).

STEP D: syn isomer of 3-acetoxymethyl-7-[2-(2-amino-4-thiazolyl)-2-hydroxyimino-acetamido]-ceph-3-eme-4-carboxylic acid The product of Step C was dissolved in 15 ml of pure trifluoroacetic acid and the mixture stood for 15 minutes and was then diluted with 100 ml of isopropyl ether. The mixture was stirred for 5 minutes and was vacuum filtered and the filter was rinsed with isopropyl ether. The product was dried and then dissolved in 2 ml of ethanol containing 0.2 ml of pyridine. The mixture was vacuum filtered and the recovered product was rinsed twice with ethanol to obtain the syn isomer of 3-acetoxymethyl-7-[2-(2-amino-4-thiazolyl)-2-hydroxyimino-acetamido]-ceph-3-eme-4-carboxylic acid RMN Spectrum (CD₃)₂SO

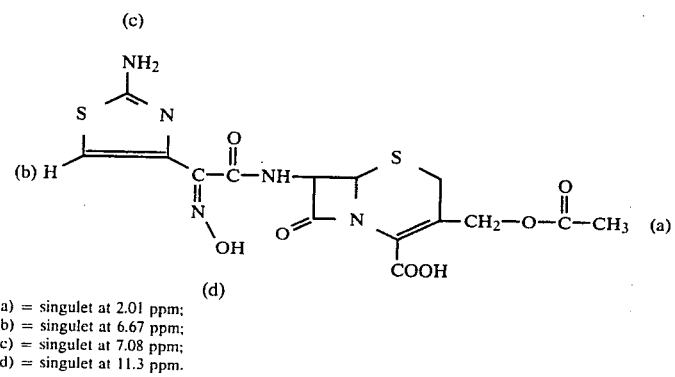

(a) = singulet at 2.01 ppm;
(b) = singulet at 6.67 ppm;
(c) = singulet at 7.08 ppm;
(d) = singulet at 11.3 ppm.

EXAMPLE 6 syn isomer of 3-acetoxymethyl-7-[2-(2-amino-4-thiazolyl)-2-hydroxyimino-acetamido]-ceph-3-eme-4-carboxylic acid STEP A: syn isomer of tert.-butyl 3-acetoxymethyl-7-[2-(2-tritylamino-4-thiazolyl)-2-(1-methyl-1-methoxy-ethoxyimino)-acetamido]-ceph-3-eme-4-carboxylate The syn isomer of 2-(2-tritylamino-4-thiazolyl)-2-(1-methyl-1-methoxy-ethoxyimino)-acetic acid of Example 1 was dissolved in 120 ml of methylene chloride and 9.84 g of tert.-butyl 7-amino-cephalosporanate were added thereto. The mixture was cooled to 10° C. and 6.6 g of dicyclohexylcarbodiimide were added thereto. The mixture was removed from the ice bath and the temperature was then allowed to rise over 3 hours to room temperature. The mixture was vacuum filtered to remove 4 g of dicyclohexylurea and the filtrate was evaporated to dryness. The residue was dissolved in 25 ml of ethyl acetate and 100 ml of ether were added thereto. The mixture was washed with 100 ml of 0.2N hydrochloric acid, with 100 ml of water and 20 ml of a molar sodium bicarbonate solution. The mixture was vacuum filtered and dried to obtain 3.9 g of the sodium salt of the starting acid. The filtrate was washed with water, dried and evaporated to dryness. The residue was taken up in 50 ml of ether and crystallization was effected by addition of 50 ml of isopropyl ether. The mixture was vacuum filtered and the recovered product was washed and dried to obtain 10.8 g of the syn isomer of tert.-butyl 3-acetoxy methyl-7-[2-(2-tritylamino-4-thiazolyl)-2-(1-methyl-1-methoxy-ethoxyimino)-acetamido]-ceph-3-eme-4-carboxylate melting at ≃160° C.

RMN Spectrum (CDCl₃):

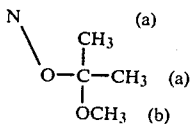

(a) = 1.53 ppm;
(b) = 3.26 ppm; 6.76 ppm (thiazole proton).

STEP B: syn isomer of tert.-butyl 3-acetoxymethyl-7-[2-(2-tritylamino-4-thiazolyl)-2-hydroxyimino-acetamido]-ceph-3-eme-4-carboxylate A solution of 0.812 g of the product of Step A in 4 ml of acetone and 1 ml of N hydrochloric acid was stirred at room temperature for 3 hours and then 1 ml of a aqueous molar solution of sodium bicarbonate was added thereto followed by addition of 10 ml of water and 5 ml of ethyl acetate to obtain 0.551 g of the syn isomer of tert.-butyl 3-acetoxymethyl-7-[2-(2-tritylamino-4-thiazolyl)-2-hydroxyimino-acetamido]-ceph-3-eme-4-carboxylate melting at ≃200° C.

Analysis: $C_{38}H_{37}O_7N_5S_2$; Calculated: %C 61.69; %H 5.04; %N 9.47; %S 8.66; Found: 61.5; 5.0; 9.1; 8.4.

RMN Spectra (CDCl₃ - 60 MHz: 1.55 ppm (tert.-butyl); 6.88 ppm (thiazole proton).

STEP C: syn isomer of 3-acetoxymethyl-7-[2-(2-amino-4-thiazolyl)-2-hydroxyimino-acetamido]-ceph-3-eme-4-carboxylic acid Using the procedure of Step D of Example 5, 0.551 g of the product of Step B and 5 ml of trifluoroacetic acid were reacted to obtain a product identical to that of Example 5.

EXAMPLE 7 syn isomer of 3-acetoxymethyl-7-[2-(2-amino-4-thiazolyl)-2-hydroxyimino-acetamido]-ceph-3-eme-4-carboxylic acid STEP A: syn isomer of diethylamine 3-acetoxymethyl-7-[2-(2-tritylamino-4-thiazolyl)-2-hydroxyimino-acetamido]-ceph-3-eme-4-carboxylate A solution of 7.6 g of the syn isomer of diethylamine 3-acetoxymethyl-7-[2-(2-tritylamino-4-thiazolyl)-2-(1-methyl-1-methoxy-ethoxyimino)-acetamido]-ceph-3-eme-4-carboxylate in 30 ml of acetone and 10 ml of 2N hydrochloric acid was stirred for 40 minutes at room temperature and then 20 ml of water were added thereto. The acetone was evaporated at 30° C. under reduced pressure and 25 ml of ethyl acetate were added thereto. The mixture was decanted and extracted and the organic phase was washed with water, dried and vacuum filtered. 1 ml of diethylamine was added to the filtrate and the mixture was triturated and iced. The mixture was vacuum filtered and the recovered product was washed with ether to obtain 6 g of pure syn isomer of diethylamine 3-acetoxymethyl-7-[2-(2-tritylamino-4-thiazolyl)-2-hydroxy-imino-acetamido]-ceph-3-eme-4-carboxylate.

Analysis: $C_{38}H_{40}O_7N_6S_2$: Calculated: % C 60.30; % H 5.33; % N 11.10; % S 8.47; Found: 60.5; 5.7; 10.9; 8.2.

RMN Spectrum (CD₃)₂SO: 6.63 ppm (thiazole proton); 7.33 ppm (trityl).

STEP B: syn isomer of 3-acetoxymethyl-7-[2-(2-amino-4-thiazolyl)-2-hydroxyimino-acetamido]-ceph-3-eme-4-carboxylic acid A mixture of 6 g of the product of Step A in 18 ml of 50% aqueous formic acid was heated at 45° C. for 15 minutes and was then vacuum filtered to remove triphenyl carbinol. The filtrate was evaporated to dryness under reduced pressure and the residue was taken up several times in ethanol to obtain the syn isomer identical to the products of Examples 5 and 6.

EXAMPLE 8 syn isomer of 3-acetoxymethyl-7-[2-(2-amino-4-thiazolyl)-2-hydroxyimino-acetamido]-ceph-3-eme-4-carboxylic acid A mixture of 8.29 g of the diethylamine salt of Step A of Example 5 and 24 ml of 50% aqueous formic acid was heated at 45° C. for 15 minutes and was then vacuum filtered to remove triphenyl carbinol. The filtrate was evaporated to dryness under reduced pressure and the residue was taken up in ethanol several times to obtain 3.5 g of a product identical to that of Examples 5,6 and 7.

EXAMPLE 9 syn isomer of 3-[(5-methyl-1,3,4-thiadiazol-2-yl)-thiomethyl]-7-[2-(2-amino-4-thiazolyl)-2-hydroxyimino-acetamido]-ceph-3-eme-4-carboxylic acid STEP A: syn isomer of diethylamine 3-[(5-methyl-1,3,4-thiazol-2-yl)-thiomethyl]-7-[2-(2-tritylamino-4-thiazolyl)-2-(1-methyl-1-methoxy-ethoxyimino)-acetamido]-ceph-3-eme-4-carboxylate 1.002 g of the syn isomer of 2-(2-tritylamino-4-thiazolyl)-2-(1-methyl-1-methoxy-ethoxyimino)-acetic acid was added to 3 ml of methylene chloride at 20° C. and then 0.23 g of dicyclohexylcarbodiimide were added thereto under nitrogen at 20° C. The mixture was stirred at 20°-25° C. for one hour to obtain a suspension of dicyclohexylurea. A mixture of 0.344 g of 3-[(5-methyl-1,3,4-thiadiazol-2-yl)-thiomethyl]-7-amino-ceph-3-eme-4-carboxylic acid and 2 ml of nitromethane was prepared and 0.28 ml of triethylamine was added to the mixture at 20°-25° C. to obtain a brown solution to which was added the suspension of dicyclohexylurea with stirring over 5 minutes at 20°-25° C. The mixture was rinsed with methylene chloride and was stirred for 2 hours and was vacuum filtered to remove 0.2 g of dicyclohexylurea. The filter was rinsed with methylene chloride and the filtrate was stirred with 8 ml of aqueous N hydrochloric acid. The mixture was vacuum filtered and the brown product was rinsed with water and methylene chloride to obtain 0.4 g of the starting carboxylic acid.

The organic filtrate was washed with distilled water until the wash waters were neutral, was dried and evaporated to dryness under reduced pressure. The residue was taken up in 5 ml of ethyl acetate and the mixture was vacuum filtered. The filter was rinsed with ethyl acetate on which there was 0.32 g of the syn isomer of 2-(2-tritylamino-4-thiazolyl)-2-hydroxyimino-acetic acid. The filtrate was concentrated to 4 ml and 0.1 ml of diethylamine were added thereto. The mixture was diluted with 9 ml of isopropyl ether at 20° C. and the mixture was stirred at 20°-25° C. and was then vacuum filtered. The product was rinsed with ethyl acetate and isopropyl ether. The filtrate was dried and evaporated to dryness under reduced pressure to obtain 0.72 g of the syn isomer of diethylamine 3-[(5-methyl-1,3,4-thiadiazol-2-yl)-thiomethyl]-2-[(1-methyl-1-methoxy-ethoxyimino)-acetamido]-ceph-3-eme-4-carboxylate.

RMN Spectrum (CDCl$_3$ - 60 MHz): 6.76 ppm (5-proton of thiazole); 7.28 (trityl protons).

STEP B: syn isomer of 3-[(5-methyl-1,3,4-thiadiazol-2-yl)-thiomethyl]-7-[2-(2-tritylamino-4-thiazolyl)-2-hydroxy-imino-acetamido]-ceph-3-eme-4-carboxylic acid 8.6 ml of 2 N hydrochloric acid were added at 20°-25° C. to a solution of 6.93 g of the product of Step A in 28 ml of acetone and the mixture was stirred for 2½ hours at 20°-25° C. Then, 4.3 ml of 2 N aqueous hydrochloric acid and 28 ml of distilled water were added thereto and the acetone was evaporated at 35° C. under reduced pressure. The mixture was vacuum filtered at room temperature and the recovered product was washed until the wash water was neutral and dried under reduced pressure to obtain 5.79 g of raw product. 2.79 g of the said product were dissolved in 8.4 ml of methylene chloride and 28 ml of ethyl acetate were added thereto at 20°-25° C. over 5 minutes. The mixture was stirred for 30 minutes and was vacuum filtered and the recovered product was rinsed with ethyl acetate and dried under reduced pressure to obtain 2.22 g of the syn isomer of 3-[(5-methyl-1,3,4-thiadiazol-2-yl)-thiomethyl]-7-[2-(2-tritylamino-4-thiazolyl)-2-hydroxy-yimino-acetamido]-ceph-3-eme-4-carboxylic acid. Concentration of the filtrate to a volume of 5 ml resulted in a second yield of 0.27 g of the said syn isomer.

RMN Spectrum (CDCl$_3$ - 60 MHz): 7.01 ppm (5-proton of thiazole); 7.31 (trityl protons).

STEP C: syn isomer of 3-[(5-methyl-1,3,4-thiadiazol-2-yl)-thiomethyl]-7-[2-(2-amino-4-thiazolyl)-2-hydroxy-yimino-acetamido]-ceph-3-eme-4-carboxylic acid A mixture of 2.48 g of the product of Step B in 7.5 ml of formic acid containing 33% water was stirred under nitrogen at 45°-50° C. for 15 minutes and 2.5 ml of distilled water were added at 45°-50° C. The mixture was vacuum filtered at 50° C. to remove 0.77 g of triphenyl carbinol and the filter was rinsed 3 times with 2.5 ml of 50% aqueous formic acid. The filtrate was evaporated to dryness under reduced pressure and the residue was triturated with 5 ml of distilled water. The mixture was vacuum filtered at 20° C. and the product was rinsed with distilled water, then with ether and dried under reduced pressure to obtain 1.06 g of the syn isomer of 3-[(5-methyl-1,3,4-thiadiazol-2-yl)-thiomethyl]-7-[2-(2-amino-4-thioazolyl)-2-hydroxyimino-acetamido]-ceph-3-eme-4-carboxylic acid.

RMN Spectrum (DMSO - 60 MHz): 6.7 ppm (5-proton of thiazole); 2.68 (methyl of thiadiazole).

EXAMPLE 10 syn isomer of sodium 3-[(5-methyl-1,3,4-thiadiazol-2-yl)-thiomethyl]-7-[2-(2-amino-4-thiazolyl)-2-hydroxyimino-acetamido]-ceph-3-eme-4-carboxylate A mixture of 1 g of the product of Example 9, 15 ml of methanol and 2.2 ml of 1 mole of triethylamine in methanol was stirred for 5 minutes and was then vacuum filtered to remove 0.066 g of insolubles. The filter was rinsed with methanol and the filtrate was admixed with 3 ml of a methanol solution of sodium acetate. The sodium salt immediately precipitated and 50 ml of ethanol were added thereto. The mixture was stirred at room temperature for 15 minutes and was then vacuum filtered. The recovered product was rinsed 3 times with 2 ml of ethanol, 3 times with 5 ml of ether and dried under reduced pressure to obtain 0.511 g of the syn isomer of sodium 3-[(5-methyl-1,3,4-thiadiazol-2-yl)-thiomethyl]-7-[2-(2-amino-4-thiazolyl)-2-hydroxyimino-acetamido]-ceph-3-eme-4-carboxylate. The filtrate was concentrated under reduced pressure to a volume of 15 ml and was vacuum filtered. The product was rinsed 3 times with 0.5 ml of ethanol and 3 times with 5 ml of ether and was dried under reduced pressure to obtain 0.200 g of the said sodium salt. The combined products were empasted for 30 minutes with 7 ml of ethanol and was vacuum filtered. The product was rinsed with ethanol, then with ether and dried under reduced pressure to obtain 0.679 g of the said sodium salt.

RMN Spectrum (DMSO - 60 MHz): 2.66 ppm (methyl of thiadiazole); 6.65 ppm (5-proton of thiazole).

EXAMPLE 11

Injectable solutions were prepared containing 500 mg of the syn isomer of sodium 3-methyl-7-[2-(2-amino-4-thiazolyl)-2-hydroxyimino-acetamido]-ceph-3-eme-4-carboxylate or the syn isomer of 3-[(1-methyl-tetrazol-5-yl)-thiomethyl]-7-[2-(2-amino-4-thiazolyl)-2-hydroxyimino-acetamido]-ceph-3-eme-4-carboxylic acid or the syn isomer of 3-acetylthiomethyl-7-[2-(2-amino-4-thiazolyl)-2-hydroxyimino-acetamido]-ceph-3-eme-4-carboxylic acid and the sufficient sterile water to obtain a final volume of 5 ml.

Gelules were also prepared containing 250 mg of the syn isomer of 3-[(1-methyl-tetrazol-5-yl)-thiomethyl]-7-[2-(2-amino-4-thiazolyl)-2-hydroxyimino-acetamido]-ceph-3-eme-4-carboxylic acid and sufficient excipient for a final weight of 400 mg.

PHARMACOLOGICAL DATA

In vitro Activity

The method used was a dilution of a liquid medium where a series of tubes received the same quantity of a sterile nutritive media and increasing doses of the test compounds were placed therein. Then, each tube was sealed with a bacterial strain and was incubated for 24 or 48 hours at 37° C. in an oven. The increasing inhibition was determined by transillumination to determine the minimum inhibiting concentration (MIC in $\mu$g/l) and the results are reported in the following Tables.

| PRODUCT OF EXAMPLE 3 | M.I.C. in µg/ml | |
|---|---|---|
| STRAINS | 24 H | 48 H |
| *Staphylococcus aureus* ATCC 6 538 Pen-Sensitive | 0,2 | 0,2 |
| *Staphylococcus aureus* UC 1 128 Pen-Resistant | 0,5 | 0,5 |
| *Staphylococcus aureus* exp. n° 54 146 | 0,2 | 0,5 |
| *Streptococcus pyogenes* A 561 | ≦0,02 | ≦0,02 |
| *Streptococcus faecalis* 5 432 | 2 | 3 |
| *Streptococcus faecalis* 99 F 74 | 5 | 20 |
| *Bacillus subtilis* ATCC 6 633 | 0,5 | 1 |
| *Escherichia Coli* Sensitive Tetracycline ATCC 9 637 | 0,1 | 0,1 |
| *Escherichia Coli* Resistant Tetracycline ATCC 11 303 | ≦0,02 | ≦0,02 |
| *Escherichia Coli* Exp. TO$_{26}$B$_6$ | 0,1 | 0,1 |
| *Escherichia Coli* Resistant Gentamicine, Tobramycine R 55 123 D | 0,1 | 0,1 |
| *Klebsiella pneumoniae* Exp. 52 145 | ≦0,02 | 0,05 |
| *Klebsiella pneumoniae* 2 536 Resistant Gentamycine | 0,5 | 0,5 |
| *Proteus mirabilis* (indol-) A 235 | 0,05 | 0,1 |
| *Salmonella typhimurium* 420 | 0,1 | 0,1 |
| *Enterobacter cloacae* 681 | 3 | 5 |
| Providencia Du 48 | 1 | 2 |
| Serratia Resistant Gentamicine 2 532 | 1 | 2 |

| PRODUCT OF EXAMPLE 4 | M.I.C. in µg/ml | |
|---|---|---|
| STRAINS | 24 H | 48 H |
| *Staphylococcus aureus* ATCC 6 538 Pen-Sensitive | 0,5 | 0,5 |
| *Staphylococcus aureus* UC 1 128 Pen-Resistant | 0,5 | 1 |
| *Staphylococcus aureus* exp. n° 54 146 | 0,5 | 1 |
| *Streptococcus pyogenes* A 561 | ≦0,02 | 0,03 |
| *Streptococcus faecalis* 5 432 | 5 | >40 |
| *Streptococcus faecalis* 99 F 74 | 10 | 40 |
| *Bacillus subtilis* ATCC 6 633 | 0,5 | 1 |
| *Escherichia Coli* Sensitive Tetracycline ATCC 9 637 | 0,5 | 0,5 |
| *Escherichia Coli* Resistant Tetracycline ATCC 11 303 | 0,2 | 0,2 |
| *Escherichia Coli* Exp. TO$_{26}$B$_6$ | 0,5 | 0,5 |
| *Escherichia Coli* Resistant Gentamycine, Tobramycine R 55 123 D | 0,5 | 0,5 |
| *Klebsiella pneumoniae* Exp. 52 145 | 0,2 | 0,5 |
| *Klebsiella pneumoniae* 2 536 Resistant Genta- | | |

| PRODUCT OF EXAMPLE 2 | M.I.C. in µg/ml | |
|---|---|---|
| STRAINS | 24 H | 48 H |
| *Staphylococcus aureus* ATCC 6 538 Pen-Sensitive | 5 | 5 |
| *Staphylococcus aureus* UC 1 128 Pen-Resistant | 5 | 5 |
| *Staphylococcus aureus* exp. n° 54 146 | 5 | 5 |
| *Streptococcus pyogenes* A 561 | 0,1 | 0,2 |
| *Streptococcus faecalis* 5 432 | 40 | 40 |
| *Streptococcus faecalis* 99 F 74 | >40 | >40 |
| *Bacillus subtilis* ATCC 6 633 | 5 | 20 |
| *Escherichia Coli* Sensitive Tetracycline ATCC 9 637 | 2 | 2 |
| *Escherichia Coli* Resistant Tetracycline ATCC 11 303 | 1 | 2 |
| *Escherichia Coli* Exp. TO$_{26}$B$_6$ | 2 | 2 |
| *Escherichia Coli* Resistant Gentamicine, Tobramycine R 55 123 D | 2 | 2 |
| *Klebsiella pneumoniae* Exp. 52 145 | 1 | 1 |
| *Klebsiella pneumoniae* 2 536 Resistant Gentamycine | 3 | 5 |
| *Proteus mirabilis* (indol-) A 235 | 1 | 2 |
| *Salmonella typhimurium* 420 | 1 | 2 |
| *Enterobacter cloacae* 681 | 10 | 20 |
| Providencia Du 48 | 10 | 40 |
| Serratia Resistant Gentamicine 2 532 | >40 | >40 |

-continued

PRODUCT OF EXAMPLE 4

| STRAINS | M.I.C. in μg/ml | |
|---|---|---|
| | 24 H | 48 H |
| mycine | 2 | 3 |
| *Proteus mirabilis* (indol-) A 235 | 0,2 | 0,2 |
| *Salmonella typhimurium* 420 | 0,5 | 0,5 |
| Providencia Du 48 | 10 | 40 |
| Serratia Resistant Gentamycine 2 532 | 20 | 40 |

PRODUCT OF EXAMPLE 10

| STRAINS | M.I.C. in μg/ml | |
|---|---|---|
| | 18 H | 24 H |
| *Staphylococcus aureus* ATCC 6 538 Pen-Sensitive | 0,5 | 0,5 |
| *Staphylococcus aureus* UC 1 128 Pen-Resistant | 0,5 | 0,5 |
| *Staphylococcus aureus* exp. n° 54 146 | 0,5 | 0,5 |
| *Staphylococcus aureus* CO 15 Resistant Cephalexine | 2 | 3 |
| *Streptococcus pyogenes* A 561 | 0,1 | 0,1 |
| *Streptococcus faecalis* 5 432 | 1 | 2 |
| *Streptococcus faecalis* 99 F 74 | 2 | 2 |
| *Bacillus subtilis* ATCC 6 633 | 0,5 | 0,5 |
| *Escherichia Coli* Sensitive Tetracycline ATCC 9 637 | 0,2 | 0,2 |
| *Escherichia Coli* Resistant Tetracycline ATCC 11 303 | ≦0,02 | ≦0,02 |
| *Escherichia Coli* Exp. TO$_{26}$B$_6$ | 0,2 | 0,2 |
| *Escherichia Coli* Resistant Gentamycine, Tobramycine R 55 123 D | 0,5 | 0,5 |
| *Klebsiella pneumoniae* Exp. 52 145 | 0,05 | 0,1 |
| *Klebsiella pneumoniae* 2 536 Resistant Gentamycine | 1 | 2 |
| *Proteus mirabilis* (indol-) A 235 | 0,1 | 0,1 |
| *Salmonella typhimurium* 420 | 0,2 | 0,2 |
| *Enterobacter cloacae* 681 | 2 | 2 |
| Providencia Du 48 | 3 | 3 |
| Serratia Resistant Gentamycine 2 532 | 3 | 4 |

B. In Vivo Activity

The product of Example 3 was studied for its activity against an experimental infection of *Proteus morganii* A-256 in groups of 10 male mice weighing about 20 g. The mice received an intraperitoneal injection of 0.5 ml of a 22 hour old culture of *Proteus morganii* A-256 in a nutritive media with a pH of 7 diluted 1/10 with distilled water. The test product was administered subcutaneously 1,5 and 24 hours after the injection and the number of dead mice was determined after 8 days. The results are reported in the following Tables.

| | MICE DEAD AFTER | | | | | | Mice living on the 8th Day |
|---|---|---|---|---|---|---|---|
| | 4h30 | 5h15 | 5h30 | 22h | 24h | 24h30 | |
| Controls | 9 | 1 | | | | | 0/10 |
| Product of Example 3 3 × 0,025 mg | 9 | | .1 | | | | 0/10 |
| Product of Example 3 3 × 0,05 mg | 3 | | | 1 | 1 | 1 | 4/10 |
| Product of Example 3 3 × 0,1 mg | | | | | | | 10/10 |

The results of the above Tables show that the compounds of the invention possess antibacterial activity.

Various modifications of the compounds and methods of the invention may be made without departing from the spirit or scope thereof and it is to be understood that the invention is intended to be limited only as defined in the appended claims.

We claim:

1. A compound of the formula

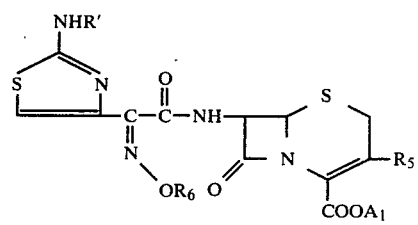

in the syn form wherein $R_5$ is —CH$_2$—S—$R_1$ where $R_1$ is selected from the group consisting of 2-methyl-1,3,4-thiadiazolyl, 1-methyl tetrazolyl and

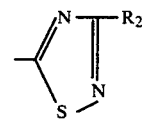

and $R_2$ is selected from the group consisting of alkyl and alkoxy of 1 to 4 carbon atoms, R' is selected from the group consisting of chloroacetyl and a group easily removable by acid hydrolysis or hydrogenolysis, $A_1$ is selected from the group consisting of hydrogen, diethylamine and an ester group easily removable by acid hydrolysis or hydrogenolysis and $R_6$ is 1-methyl-1-methoxyethyl.

2. A compound of claim 1 which is the syn isomer of 3-[(1-methyl-5-tetrazolyl)-thiomethyl]-7-[2-(2-tritylamino-4-thiazolyl)-2-(1-methyl-1-methoxy-ethoxyimino)-acetamido]-ceph-3-eme-4-carboxylic acid.

3. A compound of claim 1 which is the syn isomer of diethylamine 3-[(5-methyl-1,3,4-thiazol-2-yl)-thiomethyl]-7-[2-(2-tritylamino-4-thiazolyl)-2-(1-methyl-1-methoxy-ethoxyimino)-acetamido]-ceph-3-eme-4-carboxylate.

* * * * *